US012697375B2

(12) United States Patent
Williams

(10) Patent No.: US 12,697,375 B2
(45) Date of Patent: *Aug. 4, 2026

(54) TREATMENT OF CHRONIC OBSTRUCTIVE PULMONARY DISEASE USING BOTULINUM TOXIN

(71) Applicant: Penland Foundation, Beaumont, TX (US)

(72) Inventor: Roland M. Williams, Beaumont, TX (US)

(73) Assignee: Penland Foundation, Beaumont, TX (US)

( * ) Notice: Subject to any disclaimer, the term of this patent is extended or adjusted under 35 U.S.C. 154(b) by 747 days.

This patent is subject to a terminal disclaimer.

(21) Appl. No.: 17/987,626

(22) Filed: Nov. 15, 2022

(65) Prior Publication Data

US 2023/0071563 A1     Mar. 9, 2023

Related U.S. Application Data

(63) Continuation of application No. PCT/US2021/032116, filed on May 13, 2021.

(51) Int. Cl.
A61K 38/48          (2006.01)
A61P 11/00          (2006.01)

(52) U.S. Cl.
CPC .......... A61K 38/4893 (2013.01); A61P 11/00 (2018.01)

(58) Field of Classification Search
None
See application file for complete search history.

(56) References Cited

U.S. PATENT DOCUMENTS

| | | | |
|---|---|---|---|
| 5,766,605 A * | 6/1998 | Sanders ............. | A61K 38/4893 424/78.02 |
| 6,063,768 A | 5/2000 | First | |
| 6,139,845 A | 10/2000 | Donovan | |
| 6,143,306 A | 11/2000 | Donovan | |
| 6,261,572 B1 | 7/2001 | Donovan | |
| 6,337,075 B1 | 1/2002 | Donovan | |
| 6,632,440 B1 | 10/2003 | Quinn et al. | |
| 6,977,080 B1 | 12/2005 | Donovan | |
| 7,655,244 B2 | 2/2010 | Blumenfeld | |
| 8,470,337 B2 | 6/2013 | Manack et al. | |
| 8,734,810 B2 | 5/2014 | Blumenfeld | |
| 8,747,865 B2 | 6/2014 | Ackerman | |
| 8,852,163 B2 | 10/2014 | Deem et al. | |
| 8,972,004 B2 | 3/2015 | Simon et al. | |
| 9,254,314 B2 | 2/2016 | Finzi et al. | |
| 9,707,207 B2 | 7/2017 | Finegold | |
| 10,011,823 B2 | 7/2018 | Barbieri et al. | |
| 10,258,673 B2 | 4/2019 | Pokushalov et al. | |
| 10,722,552 B1 | 7/2020 | Williams | |
| 10,960,061 B1 | 3/2021 | Williams | |
| 10,973,873 B1 | 4/2021 | Williams | |
| 10,987,441 B1 | 4/2021 | Sykes | |

| | | |
|---|---|---|
| 11,090,371 B1 | 8/2021 | Williams |
| 2001/0012828 A1 | 8/2001 | Aoki et al. |
| 2004/0062776 A1 | 4/2004 | Voet |
| 2004/0213815 A1 | 10/2004 | Ackerman |
| 2004/0220544 A1 | 11/2004 | Heruth et al. |
| 2005/0147625 A1 | 7/2005 | First |
| 2005/0147626 A1 | 7/2005 | Blumenfeld |
| 2005/0191320 A1 | 9/2005 | Turkel et al. |
| 2007/0259002 A1 | 11/2007 | Batchelor |
| 2009/0142430 A1 | 6/2009 | Sanders et al. |
| 2009/0232850 A1 | 9/2009 | Manack et al. |
| 2010/0222286 A1 | 9/2010 | Ip et al. |
| 2010/0303788 A1 | 12/2010 | Francis et al. |
| 2011/0200639 A1 | 8/2011 | Blumenfeld |
| 2012/0093827 A1 | 4/2012 | Van Schaack et al. |
| 2012/0195878 A1 | 8/2012 | Haag-Molkenteller et al. |
| 2012/0244188 A1 | 9/2012 | Blumenfeld et al. |
| 2012/0251519 A1 | 10/2012 | Blumenfeld et al. |
| 2013/0251830 A1 | 9/2013 | Manack et al. |
| 2014/0099298 A1 | 4/2014 | Blumenfeld |
| 2015/0086533 A1 | 3/2015 | Borodic |
| 2016/0095908 A1 | 4/2016 | Borodic et al. |
| 2017/0173123 A1 | 6/2017 | Blumenfeld |
| 2017/0333537 A9 | 11/2017 | Borodic |

(Continued)

FOREIGN PATENT DOCUMENTS

| | | |
|---|---|---|
| AU | 2013202878 | 5/2013 |
| EP | 2072039 | 6/2009 |

(Continued)

OTHER PUBLICATIONS

Duke, Rebecca L; Conley, Stephen F; "Botulinum toxin as treatment for a unique case of subcutaneous emphysema" International Journal of Pediatric Otorhinolaryngology, 71, 353-356, 2007) (Year: 2007).*

Voelkel, Norbert F; et al; "COPD/emphysema: The vascular story" Pulmonary Circulation, 1, 320-326. 2011) (Year: 2011).*

Vacca et al., "Botulinum toxin A increases analgesic effects of morphine, counters development of morphine tolerance and modulates glia activation and μ opiod receptor expression in neuropathic mice," Brain, Behavior, and Immunity, 32, pp. 40-50 (2013).

Veenstra-Vanderweele et al., "Arbaclofen in Children and Adolescents with Autism Spectrum Disorder: A Randomized, Controlled, Phase 2 Trial," Neuropsychopharmacology, 42, pp. 1390-1398 (2017).

(Continued)

*Primary Examiner* — David W Berke-Schlessel
(74) *Attorney, Agent, or Firm* — Fox Rothschild LLP

(57)          ABSTRACT

Botulinum toxin for use in treating chronic obstructive pulmonary disease (COPD) in a patient in need thereof is provided. The treatment comprises administering botulinum toxin to the patient. The botulinum toxin may be administered by subcutaneous or intradermal injection. The subcutaneous or intradermal injection may be administered to and/or around the vicinity of a trigeminal nerve, a cervical nerve, a thoracic nerve, a lumbar nerve, and/or a sacral nerve of the patient.

20 Claims, No Drawings

(56) References Cited

U.S. PATENT DOCUMENTS

| 2018/0071361 A1 | 3/2018 | Abiad et al. |
| 2019/0038646 A1 | 2/2019 | Bright et al. |
| 2019/0300583 A1 | 10/2019 | Jarpe et al. |
| 2020/0239528 A1 | 7/2020 | Binz et al. |
| 2021/0060144 A1 | 3/2021 | Brooks et al. |
| 2021/0187063 A1 | 6/2021 | Williams |
| 2022/0143158 A1 | 5/2022 | Abumrad et al. |

FOREIGN PATENT DOCUMENTS

| JP | 2007509953 | 4/2007 |
| JP | 2012107051 | 6/2012 |
| KR | 20100032982 | 3/2010 |
| KR | 20150126979 | 11/2015 |
| WO | 95/28171 | 10/1995 |
| WO | 00/10598 | 3/2000 |
| WO | 2005072433 | 8/2005 |
| WO | 2010013495 | 2/2010 |
| WO | 2011084507 | 7/2011 |
| WO | 2012134897 | 10/2012 |
| WO | 2014184746 | 11/2014 |
| WO | 2018172264 | 9/2018 |
| WO | 2019126542 | 6/2019 |
| WO | 2019145577 | 8/2019 |
| WO | 2020110458 | 6/2020 |
| WO | 2022183064 | 9/2022 |

OTHER PUBLICATIONS

Wang et al., "Molecular Mechanisms of GLutamate Toxicity in Parkinson's Disease," Frontiers in Neuroscience, 14:1-12 (2020).
Webmd, "ADHD and Dyslexia: How to Tell Them Apart," available online at: <https://www.webmd.com/add-adhd/adhd-dyslexia-tell-apart?print=true>, 3 pages (2020).
WebMD, "Treatments for Dyslexia," available online at: <https://www.webmd.com/children/dyslexia-treatments?print=true>, 1 page (2020).
What-When-How, "Neuroscience," available online at: <http://what-when-how.com/neuroscience> 2 pages (2020).
Wijesekera and Leigh, "Amyotrophic lateral sclerosis," Orphanet Journal of Rare Diseases, 4(3), 22 pages (2009).
U.S. Appl. No. 17/880,962, filed Aug. 4, 2022, Botulinum Toxin for Use in Treatment.
U.S. Appl. No. 17/204,922, filed Mar. 17, 2021, Treatment of Dyslexia Using Botulinum Toxin.
U.S. Appl. No. 17/987,549, filed Nov. 15, 2022, Treatment of Asthma Using Botulinihvi Toxin.
U.S. Appl. No. 17/987,653, filed Nov. 15, 2022, Treatment of Cardiac Arrhythmia Using Botulinum Toxin.
U.S. Appl. No. 17/215,082, filed Mar. 29, 2021, Treatment of Amyotrophic Lateral Sclerosis Using Botulinum Toxin.
U.S. Appl. No. 17/987,675, filed Nov. 15, 2022, Treatment of Cirrhosis Using Botulinum Toxin.
U.S. Appl. No. 17/862,282, filed Jul. 11, 2022, Treatment of Diabetes and Chronic Pancreatitis Using Botulinum Toxin.
U.S. Appl. No. 17/862,295, filed Jul. 11, 2022, Treatment of Autism Using Botulinum Toxins.
U.S. Appl. No. 16/657,933, filed Oct. 18, 2019, Treatment of Autism Using Botulinum Toxins.
U.S. Appl. No. 17/525,367, filed Nov. 12, 2021, Botulinum Toxin for Use in Treatment of Autism Spectrum Disorders.
U.S. Appl. No. 16/995,042, filed Aug. 17, 2020, Treatment Methods Using Botulinum Toxins.
U.S. Appl. No. 16/875,912, filed May 15, 2020, Treatment of Dyslexia Using Botulinum Toxin.
U.S. Appl. No. 16/875,924, filed May 15, 2020, Treatment of Asthma Using Botulinum Toxin.
U.S. Appl. No. 16/875,935, filed May 15, 2020, Treatment of Chronic Obstructive Pulmonary Disease Using Botulinum Toxin.
U.S. Appl. No. 16/875,945, filed May 15, 2020, Treatment of Cardiac Arrhythmia Using Botulinum Toxin.
U.S. Appl. No. 16/875,947, filed May 15, 2020, Treatment of Amyotrophic Lateral Sclerosis Using Botulinum Toxin.
U.S. Appl. No. 16/875,951, filed May 15, 2020, Treatment of Cirrhosis Using Botulinum Toxin.
Simpson et al., "Practice guideline update summary: Botulinum neurotoxin for the treatment of blepharospasm, cervical dystonia, adult spasticity, and headache," Neurology, 86(19), pp. 1818-1826 (2016).
Smoot-Reinert et al., "Using Posturography to Examine the Immediate Effects of Vestibular Therapy for Children with Autism Spectrum Disorders: A Feasability Study," Phys. Occup. Ther. Pediatr., 35(4), pp. 365-380 (2015).
Hiroshi Ueda," Lysophosphatidic acid, which is responsible for inducing injury neuropathic pain," Journal of Japan Pharmacology, vol. 127, Issue 3, pp. 161-165 (2006).
Advance Nursing, "Angle of Injection," available online at: <https://nursing-skills.blogspot.com/2014/01/angle-of-injection.html>, 2 pages (2020).
Antonucci et al., "SNAP-25 a Known Presynaptic Protein with Emerging Postsynapic Functions," Frontiers in Synaptic Neuroscience, 9 pages (2016).
Chien et al., "Sympathetic Fiber Sprouting in Chronically Compressed Dorsal Root Ganglia Without Peripheral Axotomy," Author manuscript, published in final form as: J. Neuropathic Pain Symptom Palliation, 1(1), pp. 19-23, 7 pages (2005).
Children's Hospital of Pittsburgh, "Cirrhosis in Children: Symptoms and Treatment," available online at: <https://www.chp.edu/our-services/transplanUliver/education/liver-disease-states/cirrhosis>, 4 pages (2020).
Cleveland Clinic, "Glutamate," 4 pages, retrieved online:https://my.clevelandclinic.org/health/articles/22839-glutamate (2023).
Diel et al., "Photophobia and sensations of dryness in migraine patients occur independent of baseline tear vol. and improve following botulinum toxin A injections," Author manuscript, published in final form as: Br. J. Ophthalmol., 103(8), pp. 1024-1029, 15 pages (2019).
Dobrek and Thor, "Glutamate NMDA Receptors in Pathophysiology and Pharmacotherapy of Selected Nervous System Dseases," Postepy Hig Med Dosw (online), 65, pp. 338-346 (2011).
Doherty, "The Link Between Migraines and Tinnitus, Buzzing or ringing in your ears could be related to your episodes," available online at: https://www.verywellhealth.com/link-between-migraines-and-tinnitus-4077631>, 13 pages (2019).
Espinosa-Sanchez and Lopez-Escamez, "New insights into pathophysiology of vestibular migraine," Frontiers in Neurology, 6(12), pp. 1-6 (2015).
Farnsworth, "What to know about glutamate," Medical News Today (medicalnewstoday.com), 34 pages (2022).
Fernandez-Rodriguez et al., "Plasma Levels of Substance p. in Liver Cirrhosis: Relationship to the Activation of Vasopressor Systems and Urinary Sodium Excretion," Hepatology, 21, pp. 35-40 (1995).
Fleischmann et al., "Nitrous oxide may not increase the risk of cancer recurrence after colorectal surgery: a follow-up of a randomized controlled trial," BMC Anesthesiology, 9 pages (2009).
Glatte et al., "Architecture of the Cutaneous Autonomic Nervous System," Frontiers in Neurology, 10(970), pp. 1-11 (2019).
Harley Academy, "Understanding Different Types of Botulinum Toxin A," 5 pages (2021).
Hart et al., "Chronic Pancreatitis: Managing a Difficult Disease," Am. J. Gastroenterol., 115(1), pp. 49-55 (2020).
Harvard Health Publishing, "Cardiac Arrhythmias, What is it?" available online at: <https://www.health.harvard.edu/a_to_z/cardiac-arrhythmias-a-to-z>, 5 pages (2019).
Herner et al., "Glutamate increases pancreatic cancer cell invasion and migration via AMPA receptor activation and Kras-MAPK signaling," Int. J. Cancer, 129(10), pp. 2349-2359 (2011).
Hulme and Snowling, "Reading disorders and dyslexia," Curr. Opin. Pediatr., 28, pp. 731-735 (2016).
Kandel et al., "Principles of Neurai Science," Third Edition, by Simon & Schuster, p. 218 (1991).

(56) References Cited

OTHER PUBLICATIONS

Kumar, "The Emerging Role of Botulinurn Toxin in the Treatment of Orofacial Disorders: Literature Update," Asian J. Pharm. Clin. Res., 10(9), pp. 21-29 (2017).

LeWitt and Trosch, "Idiosyncratic Adverse Reactions to Intramuscular Botulinum Toxin Type A Injection," Movement Disorders, 12(6), pp. 1054-1067 (1997).

Lim and Sheet, "Botulinum toxin, Quo Vadis?," Medical Hypotheses, 69, pp. 718-723 (2007).

Mayo Clinic, "Autism Spectrum Disorder," available online at: <https://www.mayoclinic.org/diseases-conditions/autism-spectrum-disorder/symptoms-causes/syc-20352928?p=1, 5 pages (2019).

Mayo Clinic, "Epilepsy," available online at: <https://www.mayoclinic.org/diseases-conditions/epilepsy/diagnosis-treatment/drc-20350098>, 8 pages (2022).

Mazzone and Undem, "Vagal Afferent Innervation of the Airways in Health and Disease," Physiol. Rev., 96, pp. 975-1024 (2016).

Mitchell and Borasio, "Amyotrophic lateral sclerosis," Lancet 369, pp. 2031-2041 (2007).

Monroy et al., "The Use of Botulinum Toxin—A in the Treatment of Severe Bruxism in a Patient with Autism: A Case Report," Special Care in Dentistry, 26(1), pp. 37-39 (2006).

Morin, "Reading skills at different ages," 3 pages, retrieved Online: https://www.understood.org/en/articles/reading-skills-what-to-expect-at- different-ages (2014).

Mortazavi et al., "Xerostomia Due to Systemic Disease: A Review of 20 Conditions and Mechanisms," Ann. Med. Health Sci. Res., 4(4), pp. 503-510 (2014).

Nair et al., "Impaired thalamocortical connectivity in autism spectrum disorder: a study of functional and anatomical connectivity," Brain, A Journal of Neurology, 136, pp. 1942-1955 (2013).

National Institutes of Health, "Juvenile Amyotrophic Lateral Sclerosis," found online at: <https://rarediseases.info.nih.govtdiseasesi11901/juvenile- amyotrophic-lateral-sclerosis>, 8 pages (2020).

Nemmi et al., "Connectivity of the Human Number Form Area Reveals Development of a Cortical Network for Mathematics," Front. Hum. Neurosci., 2 pages (2018).

Niebroj-Dobosz and Janik, "Amino acids acting as transmitters in amyotrophic lateral sclerosis (ALS)," Acta Neural. Scand., 100, pp. 6-11 (1999).

Oomens and Forouzanfar, "Pharmaceutical Management of Trigeminal Neuraigia in the Elderly," Drugs Aging, 32, pp. 717-726 (2015).

Panju et al., "Atypical Sympathetic Arousal In Children with Autism Spectrum Disorder and Its Association with Anxiety Symptomatology," Molecular Autism, 6(64), 10 pages (2015).

Park and Park, "Botulinum Toxin for the Treatment of Neuropathic Pain," Toxins, 9(260), 15 pages (2017).

Powell et al., "The Role of CGRP in Tile Development of Morphine Tolerance and Physical Dependence," 4th International Meeting on Calcitonin Gene-Related Peptide (CGRP), The Scientific World 1(S1), 1 page (2001).

Pugh et al., "Glutamate and choline levels predict individual differences in reading ability in emergent readers," J. Neurosci., 34(11), pp. 4082-4089 (2014).

Ristic, "7 Proven Roles of Substance P and Its Associated Diseases," available online at: https://supplements.selfdecode.com/blog/substance-p-roles/>, 9 pages (2021).

Rojas, "The role of glutamate and its receptors in autism and the use of glutamate receptor antagonists in treatment," Author manuscript, published in final form as: J. Neural. Transm., 121(8), pp. 891-905 (2014 ).

Sadick, "Botulinum toxin type B," (Abstract) Dermatol. Surg., 29(4), pp. 348-350 (2003).

Sarawagi et al., "Glutamate and GABA Homeostasis and Neurometabolism in Major Depressive Disorder," Frontiers in Psychiatry, 12(637863), pp. 1-16 (2021).

Saunte and Christensen, "Improvement in reading symptoms following botulinum toxin A injection for convergence insufficiency type intermittent exotropia," Acta Opthalmologica 93(5), pp. e391-e392 (2015).

Scott and Fryer, "Role of Parasympathetic Nerves and Muscarinic Receptors in Allergy and Asthma," Author manuscript, published in final form as: Chem. Immunol. Allergy, 98, pp. 48-69 (2012).

Shimmura et al., "Alteration of Plasma Glutamate and Glutamine Levels in Children with High-Functioning Autism," PLoS ONE, 6(10), 6 pages (2011).

Shonkoff JP, Phillips DA, editors "From Neurons to Neighborhoods: The Science of Early Childhood Development," National Research Council (US) and Institute of Medicine (US) Committee on Integrating the Science of Early Childhood Development, 25 pages (2000).

Smith, "Hyperhidrosis," Vascular Surgery, 31(5), pp. 251-255 (2015).

Squires et al., "The Use of Botulinum Toxin Injections to Manage Drooling in Amyotrophic Lateral Sclerosis/Motor Neurone Disease: A Systematic Review," Dysphagia, 29, pp. 500-508 (2014).

Strobl et al., "Best Clinical Practice in Botulinum Toxin Treatment for Children with Cerebral Palsy," Toxins, 7, pp. 1629-1648 (2015).

Trizna, "Dermatologic Use of Botulinum Toxin," available online at emedicine.medscape.com; 10 pages (2019).

Alivia Nyhan, "Types of cirrhosis and their causes," 9 pages (2021).

Avery, "Botulinum Toxin for Atrial Fibrillation? Maybe, But More Study is Needed," Duke Health, Webpage, Published Nov. 15, 2017, https://corporate.dukehealth.org/news/botulinum-toxin-atrial-fibrillation-maybe-more-study-needed, Accessed: Apr. 2025. (Year: 2017).

Duke and Conley, "Botulinum toxin as treatment for a unique case of subcutaneous emphysema," International Journal of Pediatric Otorhinolaryngology, 71, pp. 353-356 (2007).

Gonzalez Eslait et al., "Implementation outcomes of a sensory integration therapy program with computerized dynamic posturography in patients with balance and sensory dysfunction," J. Otol., 18(1):26-32 (2022).

Kumar et al., "Therapeutic use of Botulinum toxin in pain treatment," Neuronal Signal, 2(3), 18 pages (2018).

Michaels et al., "Serum Levels of Substance P Are Elevated in Patients With Sickle Cell Disease and Increase Further During Vaso-Occlusive Crisis," Blood, 92:9, pp. 3148-3151 (1998).

Moyer et al., "Botulinum Toxin Type B: Experimental and ClinicalExperiance," Therapy with Botulinum Toxin. (Ed) J. Jankovic et al. Marcel Dekker, Inc., New York, pp. 71-85 (1994).

Nockher and Renz, "Neirotrophins and asthma: Novel insight into neuroimmune interaction," Journal of Allergy and Clinical Immunology, 117(1), pp. 67-71 (2006).

Park et al., "Elevated serum substance P level as a predictive marker for moderately emetognic chemotherapy- induced nausea and vomiting: A prospective cohort study," Cancer Medicine, 10, pp. 1057-1065 (2021).

Pokushalov et al., "Long-Term Suppression of Atrial Fibrillation by Botulinum Toxin Injection Into Epicardial Fat Pads in Patients Undergoing Cardiac Surgery One-Year Follow-Up of a Randomized Pilot Study," Circulation: Arrhythmia and Electrophysiology, vol. 8, Issue 6, pp. 1334-1341. (Year: 2015).

Purkiss et al., "A Method for the Measurement of CHI-Glutamate Release from Cultured Dorsal Root Ganglion Neurons," Biochemical Society Transactions, vol. 26, Article 140, page S108 (1998).

Voelkel et al., "COPD/emphysema: The vascular story," Pulmonary Circulation, 1, pp. 320-326 (2011).

Zajonc and Roland, "Vetrigo and motion sickness. Part II: Pharmacological treatment," ENT-Ear, Ear, Nose & Throat Journal, vol. 85, No. 1, pp. 25-35 (2006).

* cited by examiner

TREATMENT OF CHRONIC OBSTRUCTIVE PULMONARY DISEASE USING BOTULINUM TOXIN

This Application is a Continuation of Application PCT/US2021/032116 filed on May 13, 2021, which claims priority to U.S. application Ser. No. 16/875,935, filed May 15, 2020, entitled "Treatment of Chronic Obstructive Pulmonary Disease Using Botulinum Toxins", now U.S. Pat. No. 10,987,411 B1, issued on Apr. 27, 2021, the entirety of which is incorporated by reference.

FIELD OF THE INVENTION

The present invention generally relates to methods for diagnosing and treating (including alleviating and/or preventing) chronic obstructive pulmonary disease (COPD) and improving the COPD symptoms of children and adults.

BACKGROUND OF THE INVENTION

Botulinum toxins cleave and destroy a protein called synaptosomal nerve-associated protein 25 ("SNAP25") and/or synaptobrevin (also called vesicle-associated membrane protein ["VAMP"]). Botulinum toxins A, C, and E cleave SNAP25 at different locations, but the fleet is in general the same—the protein is destroyed and cannot function until the cell makes new ones. Botulinum toxins B, D, F and G cleave VAMP present at the cytoplasmic surface of the synaptic vesicle. The two important locations in the body where the proteins are found are at the terminals of the motor neurons (muscle) and in the cell membranes of astrocytes, glial cells, and satellite cells. These three cell types surround sensory neurons and form part of the blood-brain barrier. In motor nerves, to cause them to fire, vesicles of acetylcholine move from inside the motor neuron across the cell membrane at the synapse between the motor nerve and muscle fiber. Acetylcholine is released into the synapse and activates receptors in the muscle fiber, which contracts the muscle fiber. In sensory nerves, when a nerve is damaged from physical or mental injuries, the three aforementioned structural cells produce large amounts of Substance P, Calcitonin Gene Related Peptide (CGRP), and glutamate internally and the molecules are moved by vesicles to the cell membrane where the SNAP25 and/or VAMP moves the molecules through the cell membrane and releases the molecules into the cerebrospinal fluid that surrounds the neurons. There, the molecules bind to the receptor on the sensory nerves, causing the neuroexcitatory effects. The molecules can also diffuse in the cerebral spinal fluid (CSF) and influence other sensory nerves to become hyperactive, a process called central sensitization.

This mechanism of cleaving the SNAP25 and/or VAMP in muscles and sensory nerves causes the only known clinical effects of botulinum, which paralyzes muscles in the motor system for 3-4 months until the cell grows a new protein. This effect has been used for decades for overactive muscles (such as to treat overactive muscles as part of cervical dystonia, blepharospasm, tic, Parkinson's, cerebral palsy, etc.), wrinkles in the face, excessive sweating, and overactive bladder.

In the sensory nerves, the mechanism has been used for migraines and depression. The effect of blocking the SNAP25 and/or VAMP in the glial, satellite, and astrocyte cells will work for 5-9 months until these cells grow new proteins. The important part of this mechanism is that the botulinum effect does not destroy cells and does not stop the normal production of or effects of acetylcholine (muscles) or Substance P, CGRP, or glutamate in sensory nerves. These facts give huge advantages over a monoclonal antibody which would eliminate all glutamate, CGRP, and Substance P. Side effects of such elimination would be disastrous. The receptor antagonists also have problems—for example, because the receptor antagonists are not site-specific, they block glutamate, Substance P, and CGRP everywhere. Too little glutamate, Substance P, and CGRP is a problem, as well as too much. It is difficult to regulate oral or I.V. doses to obtain the correct level of reduction in areas that are too high in glutamate, Substance P, and/or CGRP without over-reduction in areas with normal levels.

Small doses of botulinum toxin injected into a specific muscle can cleave SNAP25 and/VAMP to calm the muscle's overreaction or paralyze the muscle temporarily if desired. Or, if injected subcutaneously near unmyelinated sensory nerves, the botulinum toxin can stop the overproduction of the sensory neuroexcitatory compounds without affecting normal glutamate, Substance P, and CGRP production and function. It is, however, noted that botulinum toxin is highly lethal. Botulinum toxin is the most toxic poison known. One molecule of botulinum toxin destroys one protein molecule of SNAP25 and/or VAMP. A little bit goes a long way. Its production, storage and injection must be done with knowledge and care.

In particular, the mechanism of the sensory effect (stopping overproduction of glutamate, Substance P, and CGRP) is as follows: almost all nerves in the human body are surrounded by a protective coating called myelin, which protects the nerve and makes neural conduction faster. Botulinum toxin has difficulty penetrating the myelin. Just under the skin are sensory pain nerves called C-fibers, which are unmyelinated. Research has shown that very low dose botulinum toxin can penetrate these axons and diffuse up the axon to the cell body into the CSF and affect the SNAP25 and/or VAMP on the glial, satellite, and astrocyte cells. Subsequently, botulinum toxin destroys the SNAP25 and/or VAMP and prevents the release of the excess Substance P, CGRP, and glutamate, which is involved in a response mechanism to neural-injury without affecting normal glutamate, Substance P, and CGRP production, use, or receptors. An example of a malfunction with the normal nerve mechanism is an infection of a nerve by the shingles virus. The infection by the shingles virus damages the nerve but does not kill it, or there would be no feeling (numbness). This causes a spike in the production of glutamate, Substance P, and CGRP. This causes the well-known shingles pain and hypersensitivity. Over a 2-3 month period, the infection is controlled, the nerve heals, and the overproduction of the neuroexcitatory chemicals gets back to normal. However, sometimes for unknown reasons, the overproduction does not get back to normal but remains high, and severe chronic pain and hypersensitivity persists. Chronically overstimulated neurons can cause numerous problems depending on where the neurons are located. The neuroexcitatory chemicals can travel up the spinal cord to the brain in the CSF and affect neurons there. This process is called central sensitization. Depending on where glutamate, Substance P, and CGRP are produced and where the molecules travel to, the molecules can cause chronic pain, headaches, vertigo, sensitivity to light, sensitivity to touch, cold sensitivity, over-active bladder, depression, anxiety, flashbacks, mental fogginess, vasoconstriction of extremities, sleep disturbances, and perhaps the death and malformation of the developing neural architecture in children with ASD (autism).

SUMMARY OF THE INVENTION

The claimed invention is related to botulinum toxin for use in treating chronic obstructive pulmonary disease (COPD) in a patient in need thereof. The method comprises administering botulinum toxin to the patient. The botulinum toxin may be administered by subcutaneous or intradermal injection. The subcutaneous or intradermal injection may be administered to and/or around the vicinity of a trigeminal nerve of the patient. The selected trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve or a combination thereof. The sub-cutaneous or intradermal injection may be administered to and/or around the vicinity of a cervical nerve of the patient. The selected cervical nerve comprises the c-2 nerve, c-3 nerve, c-4 nerve, c-5 nerve, c-6 nerve, c-7 nerve, c-8 nerve or a combination thereof. The subcutaneous or intradermal injection may be administered by subcutaneous or intrader-mal injection to and/or around a vicinity of a thoracic nerve of the patient. The selected thoracic nerve comprises the t-2 nerve, t-3 nerve, t-5 nerve, t-6 nerve, t-7 nerve, t-8 nerve, t-9 nerve, t-10 nerve, t-11 nerve, t-12 nerve, or a combination thereof. The subcutaneous or intradermal injection may be administered to and/or around the vicinity of a lumbar nerve of the patient. The selected lumbar nerve comprises the l-1 nerve, l-2 nerve, l-3 nerve, l-4 nerve, l-5 nerve, or a combination thereof. The subcutaneous or intradermal injec-tion may be administered to and/or around the vicinity of a sacral nerve of the patient. The selected sacral nerve com-prises the ls-1 nerve, s-2 nerve, s-3 nerve, s-4 nerve, s-5 nerve, or a combination thereof. In some embodiments, the subcutaneous or intradermal injection may be administered to and/or around the vicinity of a trigeminal nerve, a cervical nerve, a thoracic nerve, a lumbar nerve, and/or a sacral nerve of the patient. Preferably, the administering for an adult who weighs about 150 lbs. comprises by subcutaneous or intra-dermal injection 2-4 units to and/or around the vicinity of an ophthalmic, maxillary, and/or mandibular nerve of the trigeminal nerve (bilateral), 2-4 units to and/or around the vicinity of the c-2 to c-3, c-4 to c-6, and/or c-7 to c-8 of the cervical nerve, about one-inch lateral to the patient's spine (bilateral), 2-4 units to and/or around the vicinity of the t-2 to t-3, t-5 to t-6, t-7 to t-9, and/or t-10 to t-12 of the thoracic nerve, about one inch lateral to the patient's spine (bilateral), 2-4 unit to and/or around the vicinity of the l-1 to l-2, l-2 to l-3, and/or l-4 to l-5 of the lumbar nerve, about one inch lateral to the patient's spine (bilateral), and/or 2-4 units to and/or around the vicinity of the s-1 to s-2, s-3 to s-4, and/or s-4 to s-5 of the sacral nerve, about one inch lateral to the patient's spine (bilateral). In some desired embodiments, the botulinum toxin used in the treatment in accordance with embodiments of the present invention comprises botulinum toxin type A, botulinum toxin type B, botulinum toxin type C, botulinum toxin type D, botulinum toxin type E, botuli-num toxin type F, botulinum toxin type G, a fragment thereof, a hybrid thereof, a chimera thereof, or a combina-tion thereof. In further embodiments, a total dosage of the botulinum toxin for an adult who weighs about 150 lbs is between about 1 unit and about 150 units. The dosage of botulinum toxin for an adult or a child is adjusted for age, weight, or a combination thereof.

DETAILED DESCRIPTION OF THE PREFERRED EMBODIMENTS

Further in relation to this, before explaining at least the preferred embodiments of the invention in greater detail, it is to be understood that the invention is not limited in its application to the details of construction and to the arrange-ments of the components set forth in the following descrip-tion. It would be understood by those of ordinary skill in the art that embodiments beyond those described herein are contemplated, and the embodiments can be practiced and carried out in a plurality of different ways. Also, it is to be understood that the terminology used herein is for the purpose of description and should not be regarded as a limiting factor.

Unless otherwise defined, the terms used herein refer to that which the ordinary artisan would understand such term to mean based on the contextual use of such term herein. To the extent that the meaning of a term used herein as understood by the ordinary artisan based on the contextual use of such term differs in any way from any particular dictionary definition of such term, it is intended that the meaning of the term as understood by the ordinary artisan will prevail.

As used herein, the term "about" means approximately or nearly and in the context of a numerical value or range set forth herein means±10% of the numerical value or range recited or claimed.

The term "treating" includes delaying, alleviating, miti-gating or reducing the intensity, progression, or worsening of one or more attendant symptoms of a disorder or condi-tion and/or alleviating, mitigating or impeding one or more causes of a disorder or condition. Treatment under the claimed invention may be a preventative treatment, prophy-lactic treatment, remission of treating or ameliorating treat-ment.

The term "therapeutically effective amount" or "therapeu-tically effective dose" refers to the amount of a composition, compound, therapy, or course of treatment that, when administered to an individual for treating a disorder or disease, is sufficient to effect such treatment for the disorder or disease. The "therapeutically effective amount" will vary depending on the composition, the compound, the therapy, the course of treatment, the disorder or disease and its severity and the age, weight, etc., of the individual to be treated.

The term "unit" refers to the amount of botulinum toxin needed to kill 50% of a group of 18-20 gm female Swiss-Webster mice given the injection intraperitoneally.

The term "vicinity of a nerve" refers to anywhere on the dermatome involved with the nerve.

In accordance with the principles of the present invention, use of botulinum toxin to treat chronic obstructive pulmo-nary disease (COPD) is provided.

Treatment of Chronic Obstructive Pulmonary Disease (COPD)

COPD is a type of obstructive lung disease characterized by long-term breathing problems and chronic poor airflow. Chronic bronchitis and emphysema are older terms used for COPD. The main symptoms include shortness of breath and cough with sputum production. COPD is a progressive disease, meaning it typically worsens over time. Eventually, everyday activities such as walking or getting dressed become difficult.

Various signs or symptoms of COPD may include, but not be limited to, 1) cough (e.g., cough that persists for more than three months each year for at least two years, in combination with sputum production and without another explanation); 2) shortness of breath (breathing that requires effort and makes one feel "out of breath."); 3) physical activity limitation (reduction in physical activity); 4) inability to breathe out completely (breathing out may take longer than breathing in); 5) sputum overproduction; and 6) acute exacerbation or sudden worsening of any said symptoms.

COPD develops as a significant and chronic inflammatory response to inhaled irritants. Chronic bacterial or viral infections may also contribute to such inflammatory state. General muscle wasting that often occurs in COPD may be partly due to inflammatory mediators released by the lungs into the blood. Some also have a degree of airway hyper-responsiveness to irritants similar to those found in asthma.

Tobacco smoking is the primary cause of COPD, with contributing factors such as air pollution and genetics. Long-term exposure to these irritants causes an inflammatory response in the lungs, resulting in narrowing of the small airways and breakdown of lung tissue. This change leads to inability to breathe out fully. As the narrowing of airways and damage to lung tissue progress, complete oxygenation of the blood does not occur and the entire body is damaged by the lack of oxygen, which ultimately results in death. The diagnosis is, for example, based on the function of lung as measured by poor airflow. In contrast to asthma, the airflow reduction does not improve much with the use of a bronchodilator.

Occupational exposure (workplace dusts, chemicals, and fumes) and pollution from indoor fires are significant causes in some countries. Typically, the exposure must occur over several decades before symptoms develop. A person's genetic makeup also affects the risk. Poorly ventilated cooking fires often fueled by coal or biomass fuels such as woods and feces, lead to indoor air pollution and are one of the most common causes of COPD. These fires have been a method of cooking and heating for nearly 3 billion people. They are still used as the main source of energy in 80% of homes in India, China, and sub-Saharan Africa. Urban air pollution is a contributing factor.

An acute exacerbation or a sudden worsening of symptoms is commonly triggered by infection or environmental pollutants, or sometimes by other factors such as improper use of medications. Infections appear to be the cause of 50-75% of cases.

For those in certain career fields, cities, and smokers, it is not easy to prevent COPD. It is important to understand that smoking cessation, safety in occupational health, and avoiding air pollution are the leading ways to prevent COPD from becoming a lifelong illness.

For those who have already experienced COPD, it is important to reduce risk factors, manage stable COPD, prevent and treat acute exacerbations, and manage associated illnesses. The only measures that have been shown to reduce mortality are smoking cessation and supplemental oxygen, as well as the influenza vaccination once a year. Pulmonary rehabilitation is a program of exercise, disease management, and counseling, which is coordinated to benefit the individual. Inhaled bronchodilators are primary medications and result in a small overall benefit. Corticosteroids are usually used in inhaled form and decrease acute exacerbations in those with either moderate or severe disease. Long-term antibiotics, specifically those from the macrolide class such as erythromycin, reduce the frequency in those who have two or more a year. Supplemental oxygen, lung transplantation or lung volume-reduction surgery may also alleviate the patient's discomfort.

One of the suspected causes of the chronic inflammation is elevated levels of the neuroexcitatory peptides such as Substance P and CGRP. Studies have shown that Substance P and CGRP are highly elevated in the blood lung tissues and sputum in COPD patients. Substance P and CGRP are thought to be involved in the tissue destruction and scarring of the lungs. The overproduction of Substance P and CGRP becomes chronic, which explains why the COPD process does not stop even after triggering factors are removed. For example, when COPD is caused by smoking, the process does not stop right away even if the smoker quits smoking.

Research shows that blood CGRP levels are significantly higher in COPD patients (15.97 ng/kg) compared to people without COPD (2.36 ng/kg). Research also shows that Substance P is significantly higher in sputum (57.3 pmol/L) and plasma (8.6 pmol/L) than people without COPD in sputum (5.9 pmol/L) and plasma (3.8 pmol/L). The plasma and sputum SP concentrate correlate with FEV1/FUC that is a test for airway obstruction. The more SP, the worse airway obstruction ($r=-0.591$ m $r=-0.642$, $P<0.05$). Substance P and CGRP are known to be overproduced by the neurostructural cells (astrocytes, glial cells, and satellite cells) during the neurological damage mechanism. Thus, it is suggested that neurogenic inflammation may be involved in the airway inflammation process and subsequent airway narrowing in COPD.

To diagnose COPD, blood levels of Substance P and CGRP could be checked at regular doctor visits. For example, the diagnosis of COPD should be considered in anyone over the age of 35 to 40 who has shortness of breath, a chronic cough, sputum production, or frequent winter colds and a history of exposure to risk factors for the disease. Spirometry is then used to confirm the diagnosis. Screening those without symptoms is generally not recommended.

If a patient is diagnosed to experience COPD, he or she can be given botulinum toxin subcutaneously or by any other injection that allows the botulinum toxin to reach the unmyelinated sensory C fiber (e.g., intradermal injection, etc.) to prevent or alleviate related symptoms and/or blood tests to assess blood levels of Substance P and CGRP. Because the sensory innervation of the lungs and bronchi comes from the vagus nerve (not the cranial nerve) and branches off spinal nerves, c-1 to t-4, the botulinum toxin injection can be given to and/or around the vicinity of a trigeminal nerve, a cervical nerve, a thoracic nerve, a lumbar nerve, and/or a sacral nerve of the patient. Preferably, it is not necessary to inject botulinum toxin to the cranial nerves because there is numerous anastomosis between the trigeminal nerves and the spinal nerves. The selected trigeminal nerve may include, but is not limited to, an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof. In the facial dermatome, botulinum toxin is injected subcutaneously to the trigeminal nerve or around the vicinity of the trigeminal nerve because the trigeminal nerve is entirely sensory. In contrast, the facial nerve supplies motor innervations to the face and has no subcutaneous axons. Thus, injecting botulinum toxin to the trigeminal nerve minimizes or eliminates muscular side effects. The selected cervical nerve may include, but is not limited to, the c-2 nerve, c-3 nerve, c-4 nerve, c-5 nerve, c-6 nerve, c-7 nerve, c-8 nerve or a combination thereof. The selected thoracic nerve may include, but is not limited to, the t-2 to t-3 nerve, t-5 to t-6 nerve, t-7 to t-9 nerve, and/or t-10 to t-12 nerve or a combination thereof. The selected lumbar nerve may include, but is not limited to, the l-1 to l-2 nerve, l-2 to l-3 nerve, and/or l-4 to l-5 nerve or a combination thereof. The sacral nerve may include, but is not limited to, the ls-1 to s-2, s-3 to s-4, and/or s-4 to s-5 or a combination thereof. For example, 2-4 units to and/or around the vicinity of an ophthalmic, maxillary, and/or mandibular nerve of the trigeminal nerve (bilateral), 2-4 units to and/or around the vicinity of the c-2 to c-3, c-4 to c-6, and/or c-7 to c-8 of the cervical nerve, about one-inch lateral to the patient's spine (bilateral), 2-4 units to and/or around the vicinity of the t-2 to t-3, t-5 to t-6, t-7 to t-9, and/or t-10 to t-12 of the thoracic nerve, about one inch lateral to the patient's spine (bilateral), 2-4 unit to and/or around the vicinity of the l-1 to l-2, l-2 to l-3, and/or l-4 to l-5 of the lumbar nerve, about one inch lateral to the patient's spine (bilateral), and/or 2-4 units to and/or around the vicinity of the s-1 to s-2, s-3 to s-4, and/or s-4 to s-5 of the sacral nerve, about one inch lateral to the patient's spine (bilateral) can be administered. While the administration site is about one-inch lateral to the patient's spine in the above embodiment, the distance can be more than 0 inches, about 01-3 inches, about 0.5-2.5 inches or about 1.0-2.0 inches. Alternatively, the distance can be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0 inches. The methods according to embodiments of the present invention are preferably applied to all or many of these locations. Depending on symptoms or conditions, the botulinum toxin used in embodiments of the present invention can be injected to a subset or subgroup of the locations described in embodiments of the present invention. In one embodiment, 3 injections of 2 units each distributed along each side of the neck in the cervical area on the trigeminal nerve, 1 injection of 2 units in the ophthalmic, maxillary, mandibular division subcutaneously and bilaterally. These dosages are for an adult who weighs about 150 lbs. The dosage for an adult or child with COPD would have to be adjusted for age, weight, or a combination thereof.

Botulinum toxin is given to lower the levels of Substance P and CGRP, and botulinum toxin normally begins to work after about three days, when injected about ½ to an inch from the spinal cord for all spinal injections. Many original studies described injections in the forearm or calf, which were found to take about 2 weeks to begin working. In contrast, when the injection is subcutaneously given near the dorsal root ganglion to reach unmyelinated C-fibers, the toxin only takes less than two weeks to reach the height of its effectiveness. This is because it is a shorter distance to diffuse into the unprotected axons to the cell body. It is important to inject botulinum toxin near the patient's spine because there is about one inch of tissue between the motor and sensory nerves there and no botulinum toxin reaches the motor nerves from the injection, which causes side effects. In other words, the only place in the body where the motor and sensory nerves do not run in close proximity is where the nerves exit the patient's spine; sensory nerves exit the dorsal root and the motor nerves exit the ventral roots. Thus, injecting botulinum toxin near the patient's spine allows the use of botulinum toxin in all dermatomes without producing muscular side effects. For example, blood levels of Substance P and CGRP can be monitored to make sure that the levels drop to normal, and the COPD symptoms can be monitored to make sure the symptoms normalize as well. When the botulinum toxin wears off, blood tests show an increase in Substance P or CGRP and/or the symptoms begin to re-develop, more botulinum toxin can be given by injection to combat this effect. If levels/symptoms fail to normalize, then perhaps a small dose of one of the Substance P and CGRP antagonists can be administered to help lower Substance P and CGRP blood levels without producing side effects. For patients, as discussed, it is possible to use the claimed method to delay, alleviate, mitigate or reduce the intensity, progression, or worsening of one or more attendant symptoms of a disorder or condition, and/or the claimed method alleviates, mitigates or impedes one or more causes of a disorder or condition.

The methods according to embodiments of the present invention are novel and inventive as they allow for a minimal amount of botulinum toxin to be injected and still cover all dermatomes with no or minimal motor involvement. By using a subcutaneous or intradermal injection that reaches the unmyelinated C-fibers, it takes a lot less botulinum toxin to absorbed into them as opposed to the myelinated nerves, and there are no motor nerves in the epithelium. Also, the injection at, for example, ½ to 1 inch from the patient's spine allows for a lower dose of botulinum toxin because there is a shorter distance to the dorsal root ganglia (approximately ¼ inch) for botulinum toxin to diffuse as compared to several feet if given in arm or leg. The site is the only place in the body where the sensory and motor nerves are not in close proximity. This combination of low dose and separation of approximately 1 inch of bone and tissue between the motor and sensory nerves should minimize or eliminate any motor side effects. Furthermore, the methods according to embodiments of the present invention does not require vagus nerve injection. The only superficial exposure of the vagus nerve is Arnold's nerve which is in the ear canal. It is a mixed motor and sensory nerve, and the motor component of it innervates the throat. If you inject botulinum toxin to or around the Arnold's nerve, you can generate speech and shallowing problems. The inventor(s) have found that there is enough anastomosis between the sensory cervical nerves, the trigeminal nerve and the vagus nerve that botulinum toxin can reach the vagus ganglia and stop the overproduction of Substance P, glutamate, and CGRP.

In general, the therapeutically effective dosage or amount can be, for example, 1-150 units depending on the patient's body weight. Preferably, the total dosage for adults is about 1-150 units. The total dosage for adults whose weight is about 150 lbs is, for example, about 50-150 units. For an adult or child, the total dosage can be adjusted to the patient's body weight, age, or a combination thereof. For toddlers (e.g., from about 1 to 5 years old), the dosage can be, for example, about 1-30 units and can be adjusted to the patient's body weight and age. This is an estimate, but 30 units is the maximum dosage that has been used safely since the 1990s in cerebral palsy infants and young children to control their severe muscle spasms.

Botulinum toxins for use according to the present invention can be stored in lyophilized vacuum dried form in containers under vacuum pressure or as stable liquids. Prior to lyophilization, the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Preferably, the botulinum neurotoxin is peripherally administered by administering it to or in the vicinity of the aforementioned nerve or to the aforementioned nerve branch or its ganglion nuclei. This method of administration permits the botulinum neurotoxin to be administered to and/or to affect select intracranial target tissues. Methods of administration include injection of a solution or composition containing the botulinum neurotoxin, as described above, and include implantation of a controlled release system that controllably releases the botulinum neurotoxin to the target trigeminal tissue. Such controlled release systems reduce the need for repeat injections. Diffusion of biological activity of botulinum toxin within a tissue appears to be a function of dose and can be graduated. Jankovic J., et al *Therapy with Botulinum Toxin*, Marcel Dekker, Inc., (1994), page 150. Thus, diffusion of botulinum toxin can be controlled to reduce potentially undesirable side effects that may affect the patient's cognitive abilities. For example, the botulinum neurotoxin may be administered so that the botulinum neurotoxin primarily effects neural systems believed to be involved in a selected neuropsychiatric disorder, and does not have negatively adverse effects on other neural systems.

In addition, the botulinum neurotoxin may be administered to the patient in conjunction with a solution or composition that locally decreases the pH of the target tissue environment. For example, a solution containing hydrochloric acid may be used to locally and temporarily reduce the pH of the target tissue environment to facilitate translocation of the neurotoxin across cell membranes. The reduction in local pH may be desirable when the composition contains fragments of botulinum neurotoxins that may not have a functional targeting moiety (e.g., a portion of the toxin that binds to a neurotoxin receptor, and/or a translocation domain). By way of example, and not by way of limitation, a fragment of botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its effects within the cell. The pH of the target tissue is only temporarily lowered so that neuronal and/or glial injury is reduced.

The botulinum toxin used in the treatment in accordance with embodiments of the present invention comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof. Because of different mechanisms and cleavage sites of botulinum toxins, the potency, dosage, or duration may vary depend on the type of botulinum toxins. The botulinum toxin can be used with other modulating drugs or chemicals. In further embodiments, the therapeutically effective amount of the botulinum toxin administered is between about 1 unit and about 150 units.

In some embodiments, a composition administered to a patient consists of botulinum toxin(s). Alternatively, a pharmaceutically active composition contained in a composition administered to a patient consists of botulinum toxin(s). The composition may additionally include, but not be limited to, a pharmaceutically inactive excipient, stabilizer and/or carrier. If lyophilized, the botulinum toxin may be reconstituted with saline or water to make a solution or composition to be administered to the patient. Alternatively, a composition administered to a patient comprises botulinum toxin(s) and other pharmaceutically active ingredients.

Illustrative embodiments are explained in the following example of a case study conducted with a patient having COPD.

Example 1

Patient is an 85-year-old male. The patient weighs about 230 lbs. He has been diagnosed with moderate to severe COPE and asbestosis. To ameliorate COPD, Brea inhaler once a day and one pill of Singulair a day were prescribed. In January, his physician tried to switch him to a different inhaler that was not as strong as Brea inhaler. Within 3 days, the patient had to go to the ER with extreme shortness of breath and was placed back on Brea. Home oxygen as needed was doing okay with occasional shortness of breath with too much exertion. On Mar. 12, 2020, he was administered botulinum toxin in the area of trigeminal, cervical, thoracic, lumbar and sacral nerves (2 units in ophthalmic, 2 units in maxillary, 2 units in mandibular of trigeminal nerve bilaterally; 2 units in the c-2-c-3, 2 units in the c-5-c-6, 2 units in the c-7-c-8 of cervical nerve bilaterally; 2 units in the t-1-t-3, 2 units in the t-5-t-6, 2 units in the t-8-t-9, 2 units in the t-11-t-12 of thoracic nerve bilaterally; 2 units in the l-1-l-2, 2 units in the l-3-l-4, 2 units in the l-4-l-5 of lumbar nerve bilaterally; 2 units in the s-1-s-2, 2 units in the s-3-s-4, 2 units in the s-5 of sacral nerve bilaterally for a total of 64 units). On Mar. 23, 2020 (11 days after injection), the patient reported that he felt so good that he can quit both the Brea and Singulair. He still felt some mucus production but it was better than before. On Mar. 30, 2020 (16 days after injection), the patient reported that he was fine with no medication. He felt like he has more energy and can do more.

Unless defined otherwise, all technical and scientific terms used herein have same meaning as commonly understood by the person of ordinary skill in the art to which this invention belongs.

It should be understood that the above description of the invention and specific examples, while indicating preferred embodiments of the present invention, are given by way of illustration and not limitation. Many changes and modifications within the scope of the present invention may be made without departing from the spirit thereof, and the present invention includes all such changes and modifications.

What is claimed is:

1. A method for treating chronic obstructive pulmonary disease (COPD) in a patient in need thereof, the method comprising administering botulinum toxin to the patient, thereby treating COPD, wherein administering for an adult comprises, by subcutaneous or intradermal injection, 1-4 units to and/or around the vicinity of a trigeminal nerve, 1-4 units to and/or around the vicinity of a cervical nerve, lateral to the patient's spine, 1-4 units to and/or around the vicinity of a thoracic nerve, lateral to the patient's spine, 1-4 units to and/or around the vicinity of a lumbar nerve, lateral to the patient's spine, and/or 1-4 units to and/or around the vicinity of a sacral nerve, lateral to the patient's spine, and monitoring whether the patient's blood level of at least one neuroexcitatory substance selected from substance P, CGRP, and glutamate normalizes.

2. The method of claim 1, wherein administering the 1-4 units to and/or around the vicinity of the trigeminal nerve comprises administering the 1-4 units to and/or around the vicinity of an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof.

3. The method of claim 1, wherein administering the 1-4 units to and/or around the vicinity of the cervical nerve comprises administering the 1-4 units to and/or around the vicinity of a C2 nerve, C3 nerve, C4 nerve, C5 nerve, C6 nerve, C7 nerve, C8 nerve, or a combination thereof.

4. The method of claim 1, wherein administering the 1-4 units to and/or around the vicinity of the thoracic nerve comprises administering the 1-4 units to and/or around the vicinity of a T2 nerve, T3 nerve, T5 nerve, T6 nerve, T7 nerve, T8 nerve, T9 nerve, T10 nerve, T11 nerve, T12 nerve, or a combination thereof.

5. The method of claim 1, wherein administering the 1-4 units to and/or around the vicinity of the lumbar nerve comprises administering the 1-4 units to and/or around the vicinity of an L1 nerve, L2 nerve, L3 nerve, L4 nerve, L5 nerve, or a combination thereof.

6. The method of claim 1, wherein administering the 1-4 units to and/or around the vicinity of the sacral nerve comprises administering the 1-4 units to and/or around the vicinity of an S1 nerve, S2 nerve, S3 nerve, S4 nerve, S5 nerve, or a combination thereof.

7. The method of claim 1, wherein the botulinum toxin comprises botulinum toxin type A, botulinum toxin type B, botulinum toxin type C, botulinum toxin type D, botulinum toxin type E, botulinum toxin type F and botulinum toxin type G, a fragment thereof, a hybrid thereof, a chimera thereof, or a combination thereof.

8. The method of claim 1, wherein each of the subcutaneous or intradermal injection is bilateral.

9. The method of claim 1, wherein a total dosage of the botulinum toxin for an adult who weighs about 150 lbs is between about 1 unit and about 150 units.

10. The method of claim 1, wherein a total dosage of the botulinum toxin for an adult or a child is adjusted for age, weight, or a combination thereof.

11. The method of claim 1, wherein the at least one neuroexcitatory substance comprises substance P.

12. The method of claim 1, wherein the at least one neuroexcitatory substance comprises CGRP.

13. The method of claim 1, wherein the monitoring if the patient's neuroexcitatory substances level normalizes comprises monitoring if the patient's blood glutamate level normalizes.

14. The method of claim 13, wherein a normal blood glutamate level is from about 40 to about 60 uM.

15. The method of claim 1, wherein if the patient's neuroexcitatory substances level fails to normalize, additional botulinum toxin is administered to the patient.

16. The method of claim 15, wherein if the patient's neuroexcitatory substances level fails to normalize even after administering the additional botulinum toxin, an antagonist to the neuroexcitatory substances is administered to the patient.

17. The method of claim 1, wherein if the patient's neuroexcitatory substances level fails to normalize, an antagonist to the neuroexcitatory substances is administered to the patient.

18. The method of claim 1, wherein the monitoring whether the patient's neuroexcitatory substances level normalizes occurs one or two weeks after the administering botulinum toxin to the patient.

19. The method of claim 1, further comprising monitoring the patient's physical symptoms.

20. The method of claim 19, wherein if the patient's physical symptom continues, additional botulinum toxin or an antagonist to the neuroexcitatory substances is administered to the patient.

* * * * *